United States Patent
Ignasiak

(10) Patent No.: US 11,666,384 B2
(45) Date of Patent: Jun. 6, 2023

(54) PREDICTION OF POSTOPERATIVE GLOBAL SAGITTAL ALIGNMENT BASED ON FULL-BODY MUSCULOSKELETAL MODELING AND POSTURE OPTIMIZATION

(71) Applicant: NuVasive, Inc., San Diego, CA (US)

(72) Inventor: Dominika Ignasiak, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 374 days.

(21) Appl. No.: 16/742,866

(22) Filed: Jan. 14, 2020

(65) Prior Publication Data

US 2020/0222121 A1 Jul. 16, 2020

Related U.S. Application Data

(60) Provisional application No. 62/792,349, filed on Jan. 14, 2019.

(51) Int. Cl.
*G06K 9/00* (2022.01)
*A61B 34/10* (2016.01)
(Continued)

(52) U.S. Cl.
CPC .............. *A61B 34/10* (2016.02); *A61B 34/25* (2016.02); *G06T 7/0012* (2013.01);
(Continued)

(58) Field of Classification Search
CPC ... A61B 34/10; A61B 34/25; A61B 2034/105; A61B 2034/107; A61B 2034/303;
(Continued)

(56) References Cited

U.S. PATENT DOCUMENTS 7,346,382 B2   3/2008 McIntyre
9,861,446 B2 *  1/2018 Lang ................ A61B 90/36
(Continued)

FOREIGN PATENT DOCUMENTS

WO   2015054543 A1   4/2015
WO   2015195843 A2   12/2015
(Continued)

OTHER PUBLICATIONS

Scheer et al., "Development of Validated Computer-based Preoperative Predictive Model for Proximal Junction Failure (PJF) or Clinically Significant PJK With 86% Accuracy Based on 510 ASD Patients With 2-year Follow-up.", Spine 41, 2016, pp. E1328-E1335.

(Continued)

*Primary Examiner* — Shervin K Nakhjavan
(74) *Attorney, Agent, or Firm* — Merchant & Gould P.C.

(57) ABSTRACT

A system for surgical planning and assessment of spinal pathology or spinal deformity correction in a subject, the system comprises a control unit configured to align one or more vertebral bodies of a biomechanical model to one or more vertebral bodies of the radiograph. The control unit is configured to receive one or more spinal correction inputs. The control unit is configured to, based on the received one or more spinal correction inputs, simulate the biomechanical model in a predetermined posture. The control unit is configured to provide for display one or more characteristics of the simulated biomechanical model.

26 Claims, 6 Drawing Sheets

(51) Int. Cl.
*A61B 34/00* (2016.01)
*G06T 7/00* (2017.01)
*A61B 34/30* (2016.01)

(52) U.S. Cl.
CPC ... *A61B 2034/105* (2016.02); *A61B 2034/107* (2016.02); *A61B 2034/303* (2016.02); *G06T 2207/10124* (2013.01); *G06T 2207/30012* (2013.01)

(58) Field of Classification Search
CPC ............ A61B 2034/104; G06T 7/0012; G06T 2207/10124; G06T 2207/30012; G16H 20/40; G16H 50/50
See application file for complete search history.

(56) References Cited

U.S. PATENT DOCUMENTS

| | | | |
|---|---|---|---|
| 11,311,222 B2 * | 4/2022 | Wybo | B25J 9/1666 |
| 2005/0043660 A1 | 2/2005 | Stark et al. | |
| 2006/0074292 A1 * | 4/2006 | Thomson | A61B 6/12 600/411 |
| 2007/0172797 A1 * | 7/2007 | Hada | G09B 23/32 434/1 |
| 2007/0288064 A1 | 12/2007 | Butson et al. | |
| 2008/0009773 A1 * | 1/2008 | Harrison | A61B 5/1079 600/595 |
| 2009/0287271 A1 | 11/2009 | Blum et al. | |
| 2010/0030232 A1 * | 2/2010 | Zehavi | A61F 2/4611 606/130 |
| 2010/0191071 A1 | 7/2010 | Anderson et al. | |
| 2010/0295848 A1 * | 11/2010 | Grewer | G06T 7/11 382/128 |
| 2011/0054870 A1 | 3/2011 | Dariush et al. | |
| 2012/0014580 A1 | 1/2012 | Blum et al. | |
| 2012/0041562 A1 | 2/2012 | Shachar et al. | |
| 2012/0265268 A1 | 10/2012 | Blum et al. | |
| 2013/0131486 A1 * | 5/2013 | Copf | G09B 23/30 600/407 |
| 2013/0173240 A1 | 7/2013 | Koell et al. | |
| 2013/0218163 A1 | 8/2013 | Frey | |
| 2013/0325069 A1 | 12/2013 | Pereiro de Lamo et al. | |
| 2014/0228860 A1 * | 8/2014 | Steines | A61B 34/10 606/130 |
| 2014/0244220 A1 * | 8/2014 | McKinnon | G06F 30/00 703/1 |
| 2015/0100091 A1 | 4/2015 | Tohmeh et al. | |
| 2016/0012753 A1 * | 1/2016 | Mehdian | G09B 23/34 434/274 |
| 2016/0117817 A1 * | 4/2016 | Seel | G06T 7/337 382/131 |
| 2016/0157751 A1 * | 6/2016 | Mahfouz | A61B 6/5211 600/409 |
| 2016/0235479 A1 | 8/2016 | Mosnier et al. | |
| 2016/0242857 A1 | 8/2016 | Scholl | |
| 2016/0270772 A1 | 9/2016 | Beale et al. | |
| 2016/0354161 A1 | 12/2016 | Deitz | |
| 2017/0135770 A1 | 5/2017 | Scholl et al. | |
| 2017/0231710 A1 | 8/2017 | Scholl et al. | |
| 2017/0252107 A1 * | 9/2017 | Turner | A61B 34/10 |
| 2017/0367738 A1 | 12/2017 | Scholl et al. | |
| 2019/0108645 A1 * | 4/2019 | Ben-Yishai | G06T 7/75 |
| 2019/0149797 A1 * | 5/2019 | Casas | H04N 13/296 348/47 |
| 2019/0192226 A1 * | 6/2019 | Lang | A61B 34/10 |
| 2020/0015911 A1 | 1/2020 | Yi | |
| 2022/0013211 A1 * | 1/2022 | Steinberg | G16H 20/40 |

FOREIGN PATENT DOCUMENTS

| | | |
|---|---|---|
| WO | 2017064719 A1 | 4/2017 |
| WO | 2017127838 A1 | 7/2017 |
| WO | 2018/155894 | 8/2018 |

OTHER PUBLICATIONS

Saha et al., "The effect of trunk-flexed postures on balance and metabolic energy expenditure during standing.", Spine (Phila Pa 1976) 32, 2007, pp. 1605-1611.

Farahani et al., "Prediction of the movement patterns for human squat jumping using the inverse-inverse dynamics technique.", XIII International Symposium on Computer Simulation in Biomechanics, 2011, 2 p.

Rasmussen et al. "A General Method for Scaling Musculo-Skeletal Models." In International Symposium on Computer Simulation in Biomechanics. United States.

Ahmadiet al., "Kinematic analysis of dynamic lumbar motion in patients with lumbar segmental instability using digital videofluoroscopy.", European spine journal: official publication of the European Spine Society, the European Spinal Deformity Society, and the European Section of the Cervical Spine Research Society 18, 2009, pp. 1677-1685.

Ailon et al., "Adult Spinal Deformity Surgeons Are Unable to Accurately Predict Postoperative Spinal Alignment Using Clinical Judgment Alone.", International Spine Study, G., 2016, Spine Deform 4, pp. 323-329.

Ames et al., "Impact of spinopelvic alignment on decision making in deformity surgery in adults: A review.", J Neurosurg Spine 16, 2012, pp. 547-564.

Bae et al., "Impact of Fatigue on Maintenance of Upright Posture: Dynamic Assessment of Sagittal Spinal Deformity Parameters After Walking 10 Minutes.", Spine (Phila Pa 1976), 2017, 42, pp. 733-739.

Banno et al., "Assessment of the Cross-Sectional Areas of the Psoas Major and Multifidus Muscles in Patients With Adult Spinal Deformity: A Case-Control Study.", Clin Spine Surg 30, 2017, pp. E968-E973.

Benditz et al., "Regarding loads after spinal fusion, every level should be seen separately: a musculoskeletal analysis.", Eur Spine J. 2018.

Boissiere et al., "Lumbar spinal muscles and spinal canal study by MRI three-dimensional reconstruction in adult lumbar spinal stenosis.", Orthop Traumatol Surg Res 103, 2017, pp. 279-283.

Bruno et al., "The effect of thoracic kyphosis and sagittal plane alignment on vertebral compressive loading.", Journal of bone and mineral research: the official journal of the American Society for Bone and Mineral Research, 27, 2012, pp. 2144-2151.

Bruno et al., "Spinal Loading Patterns From Biomechanical Modeling Explain the High Incidence of Vertebral Fractures in the Thoracolumbar Region.", Journal of bone and mineral research: the official journal of the American Society for Bone and Mineral Research, 32, 2017, pp. 1282-1290.

Claus et al., "Different ways to balance the spine: subtle changes in sagittal spinal curves affect regional muscle activity.", Spine (Phila Pa 1976) 34, 2009, pp. E208-E214.

Crawford et al., "Change in fatty infiltration of lumbar multifidus, erector spinae, and psoas muscles in asymptomatic adults of Asian or Caucasian ethnicities.", European spine journal: official publication of the European Spine Society, the European Spinal Deformity Society, and the European Section of the Cervical Spine Research Society 26, 2017, pp. 3059-3067.

Damsgaard et al., "Analysis of musculoskeletal systems in the AnyBody Modeling System.", Simulation Modelling Practice and Theory 14, 2006, pp. 1100-1111.

De Zee et al., "A detailed rigid-body cervical spine model based on inverse dynamics.", Journal of Biomechanics 40, Supplement 2, 2007a, p. S284.

De Zee et al., "A generic detailed rigid-body lumbar spine model.", J. Biomech 40, 2007b, pp. 1219-1227.

Dendorfer, et al., Report 21385/08/NL/PA, 2008.

Diebo et al., "Recruitment of compensatory mechanisms in sagittal spinal malalignment is age and regional deformity dependent: a full-standing axis analysis of key radiographical parameters.", Spine (Phila Pa 1976) 40, 2015, pp. 642-649.

Dijkstra et al., "Prediction of postural strategies.", Gait & Posture 42, 2015, pp. S99-S100.

(56) References Cited

OTHER PUBLICATIONS

Erdemir et al., "Model-based estimation of muscle forces exerted during movements.", Clinical Biomechanics (Bristol, Avon) 22, 2007, pp. 131-154.
Farahani et al., "Human arm posture prediction in response to isometric endpoint forces.", J Biomech 48, 2015a, pp. 4178-4184.
Farahani et al., "Optimization-based dynamic prediction of kinematic and kinetic patterns for a human vertical jump from a squatting position.", Multibody System Dynamics 36, 2015b, pp. 37-65.
Fukui, et al., "Biomechanical Analysis of Influence of Spinal Fixation on Intervertebral Joint Force by Using Musculoskeletal Model.", ICBME.
Glassman et al., "Correlation of radiographic parameters and clinical symptoms in adult scoliosis.", Spine 30, 2005a, pp. 682-688.
Glassman et al., "The impact of positive sagittal balance in adult spinal deformity.", Spine 30, 2005b, pp. 2024-2029.
Glassman et al., "Sagittal balance is more than just alignment: why PJK remains an unresolved problem.", Scoliosis Spinal Disord 11, 2016, p. 1.
Ignasiak et al., "Thoracolumbar spine model with articulated ribcage for the prediction of dynamic spinal loading.", Journal of biomechanics 49, 2016a, pp. 959-966.
Ignasiak et al., "A rigid thorax assumption affects model loading predictions at the upper but not lower lumbar levels.", Journal of Biomechanics 49, 2016b, pp. 3074-3078.
Ignasiak et al., "The influence of spinal fusion length on proximal junction biomechanics: a parametric computational study.", Eur Spine J., 2018a.
Ignasiak et al., "Multi-segmental thoracic spine kinematics measured dynamically in the young and elderly during flexion.", Human movement science 54, 2017, pp. 230-239.
Ignasiak et al., "The effect of muscle ageing and sarcopenia on spinal segmental loads.", Eur Spine J., 2018b.
Intolo et al., "The effect of age on lumbar range of motion: a systematic review.", Manual therapy 14, 2009, pp. 596-604.
Jalai et al., "The impact of obesity on compensatory mechanisms in response to progressive sagittal malalignment.", Spine J 17, 2017, pp. 681-688.
Kasai et al., "Sex- and age-related differences in mid-thigh composition and muscle quality determined by computed tomography in middle-aged and elderly Japanese.", Geriatr Gerontol Int 15, 2015, pp. 700-706.
Klein et al., "Morphological muscle and joint parameters for musculoskeletal modelling of the lower extremity.", Clin Biomech (Bristol, Avon) 22, 2007, pp. 239-247.
Lafage et al., "Virtual Modeling of Postoperative Alignment Following Adult Spinal Deformity (ASD) Surgery Helps Predict associations between Compensatory Spinopelvic Alignment Changes, Overcorrection and Proximal Junctional Kyphosis (PJK).", Spine (Phila Pa 1976), 2017a.
Lafage et al., "Defining the Role of the Lower Limbs in Compensating for Sagittal Malalignment.", Spine (Phila Pa 1976) 42, 2017b, pp. E1282-E1288.
Lafage et al., "Self-learning computers for surgical planning and prediction of postoperative alignment.", Eur Spine J 27,2018, pp. 123-128.
Lafage et al., "Changes in thoracic kyphosis negatively impact sagittal alignment after lumbar pedicle subtraction osteotomy: a comprehensive radiographic analysis.", Spine (Phila Pa 1976) 37, International Spine Study, G., 2012a, pp. E180-E187.
Lafage et al., "Multicenter validation of a formula predicting postoperative spinopelvic alignment.", J Neurosurg Spine 16, 2012b, pp. 15-21.
Lafage et al., "Pelvic tilt and truncal inclination: two key radiographic parameters in the setting of adults with spinal deformity.", Spine (Phila Pa 1976) 34, 2009, pp. E599-E606.
Lafage et al., "Spino-pelvic parameters after surgery can be predicted: a preliminary formula and validation of standing alignment.", Spine 36, 2011, pp. 1037-1045.

Malakoutian et al., "Role of muscle damage on loading at the level adjacent to a lumbar spine fusion: a biomechanical analysis.", European Spine Journal 25, 2016, pp. 2929-2937.
Ota et al., "Age-related changes in the thickness of the deep and superficial abdominal muscles in women.", Arch Gerontol Geriatr 55, 2012, pp. e26-e30.
Ploumis et al., "Ipsilateral atrophy of paraspinal and psoas muscle in unilateral back pain patients with monosegmental degenerative disc disease.", Br J Radiol 84, 2011, pp. 709-713.
Protopsaltis et al., "The T1 pelvic angle, a novel radiographic measure of global sagittal deformity, accounts for both spinal inclination and pelvic tilt and correlates with health-related quality of life.", J Bone Joint Surg Am 96, International Spine Study, G., 2014, pp. 1631-1640.
Protopsaltis et al., "The Lumbar Pelvic Angle (LPA), the Lumbar Component of the T1 Pelvic Angle, Correlates with HRQOL, PI-LL Mismatch and it Predicts Global Alignment.", Spine (Phila Pa 1976) International Spine Study, G., 2017.
Putzer et al., "A numerical study to determine the effect of ligament stiffness on kinematics of the lumbar spine during flexion.", BMC Musculoskelet Disord 17, 2016, p. 95.
Schmidt et al., "The stiffness of lumbar spinal motion segments with a high-intensity zone in the anulus fibrosus.", Spine 23, 1998, pp. 2167-2173.
Schwab et al., "Adult spinal deformity-postoperative standing imbalance: how much can you tolerate? An overview of key parameters in assessing alignment and planning corrective surgery.", Spine 35, 2010, pp. 2224-2231.
Schwab et al., "Radiographical spinopelvic parameters and disability in the setting of adult spinal deformity: a prospective multicenter analysis.", International Spine Study, G., Spine (Phila Pa 1976) 38, 2013, pp. E803-E812.
Senteler et al., "Fusion angle affects intervertebral adjacent spinal segment joint forces-Model-based analysis of patient specific alignment.", J Orthop Res 35, 2017, pp. 131-139.
Senteler et al., "Pelvic incidence-lumbar lordosis mismatch results in increased segmental joint loads in the unfused and fused lumbar spine.", Eur Spine J 23, 2014, pp. 1384-1393.
Silder et al., "Identification of passive elastic joint moment-angle relationships in the lower extremity.", J Biomech 40, 2007, pp. 2628-2635.
Teyhen et al., "Fluoroscopic video to identify aberrant lumbar motion.", Spine 32, 2007, pp. E220-E229.
Uribe et al., "Finite element analysis of lordosis restoration with anterior longitudinal ligament release and lateral hyperlordotic cage placement.", Eur Spine J 24 Suppl 3, 2015, pp. 420-426.
Van der Helm, "A finite element musculoskeletal model of the shoulder mechanism.", J Biomech 27, 1994, pp. 551-569.
Wang et al., "Quantitative MRI and X-ray analysis of disc degeneration and paraspinal muscle changes in degenerative spondylolisthesis.", Journal of back and musculoskeletal rehabilitation 28, 2015, pp. 277-285.
Wilke et al., "In vitro analysis of the segmental flexibility of the thoracic spine.", PloS one 12, e0177823, 2017.
Wong et al., "The flexion-extension profile of lumbar spine in 100 healthy volunteers.", Spine 29, 2004, pp. 1636-1641.
Wong et al., "Continuous dynamic spinal motion analysis.", Spine 31, 2006, pp. 414-419.
Yagi et al., "The paravertebral muscle and psoas for the maintenance of global spinal alignment in patient with degenerative lumbar scoliosis.", Spine J 16, 2016, pp. 451-458.
PCT International Search Report and Written Opinion in International Application PCT/US2020/013578, dated Apr. 30, 2020, 12 pages.
PCT International Preliminary Report on Patentability in International Application PCT/US2020/013578, dated Jul. 29, 2021, 9 pages.
AnyBody Publication List, located online on Sep. 29, 2022 at: https://anybodytech.com/resources/anybodypublications/, 90 pages.
AnyBody Technology, "ARO Medical breaks the degenerative spiral", ARO Medical, Version 1.3, Nov. 20, 2013, 1 page.
AnyScript.org—Wiki: AnyScript Support Wiki, Main Page, located online on the Wayback Machine on Sep. 29, 2022 at: https://web.

(56) References Cited

OTHER PUBLICATIONS archive.org/web/2016022423555/http://wiki.anyscript.org:80/index.php/Main_Page, page last modified Oct. 5, 2015, 2 pages.

* cited by examiner

PREDICTION OF POSTOPERATIVE GLOBAL SAGITTAL ALIGNMENT BASED ON FULL-BODY MUSCULOSKELETAL MODELING AND POSTURE OPTIMIZATION

CROSS-REFERENCE TO RELATED APPLICATION

This application claims the benefit of and priority to U.S. Provisional Application No. 62/792,349, filed on Jan. 14, 2019, the entire disclosure of which is incorporated herein by reference.

FIELD

This disclosure describes prediction of post-operative sagittal alignment based on simulation of a biomechanical model.

BACKGROUND

The ability to maintain an erect body posture and horizontal gaze requires adequate standing balance and normal spino-pelvic sagittal alignment. The relationships between malalignment and reduced health-related quality of life have been demonstrated in several studies, highlighting the importance of considering sagittal balance when planning spinal surgery. This applies to not only deformity but also degenerative cases, as even local malalignment can distort optimal global balance, leading to pain and disability.

SUMMARY

In one embodiment, a system for surgical planning and assessment of spinal pathology or spinal deformity correction in a subject includes a control unit, an input device and a display device. The control unit being configured to align on or more vertebral bodies of a biomechanical model to one or more vertebral bodies of the radiograph. The control unit also being configured to receive one or more spinal correction inputs. The control unit also being configured to, based on the received one or more spinal correction inputs, simulate the biomechanical model in a predetermined posture. The control unit also being configured to provide for display one or more characteristics of the simulated biomechanical model.

In another embodiment, a method for surgical planning and assessment of spinal deformity correction in a subject includes aligning one or more vertebral bodies of a biomechanical model to one or more vertebral bodies of a radiograph. The method also includes receiving one or more spinal correction inputs. The method also includes based on the received one or more spinal correction inputs, simulating the biomechanical model in a predetermined posture. The method also includes providing for display one or more characteristics of the simulated biomechanical model.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to active the developers' specific goals, such as compliance with system-related and business-related constraints, which will vary from one implementation to another. Moreover, it will be appreciated that such a development effort might be complex and time-consuming, but nevertheless be a routine undertaking for those of ordinary skill in the art having the benefit of this disclosure. It is furthermore to be readily understood that, although discussed below primarily within the context of spinal surgery, the systems and methods of the present invention may be employed in any number of anatomical settings to provide access to any number of different surgical target sites throughout the body.

Figure 1:
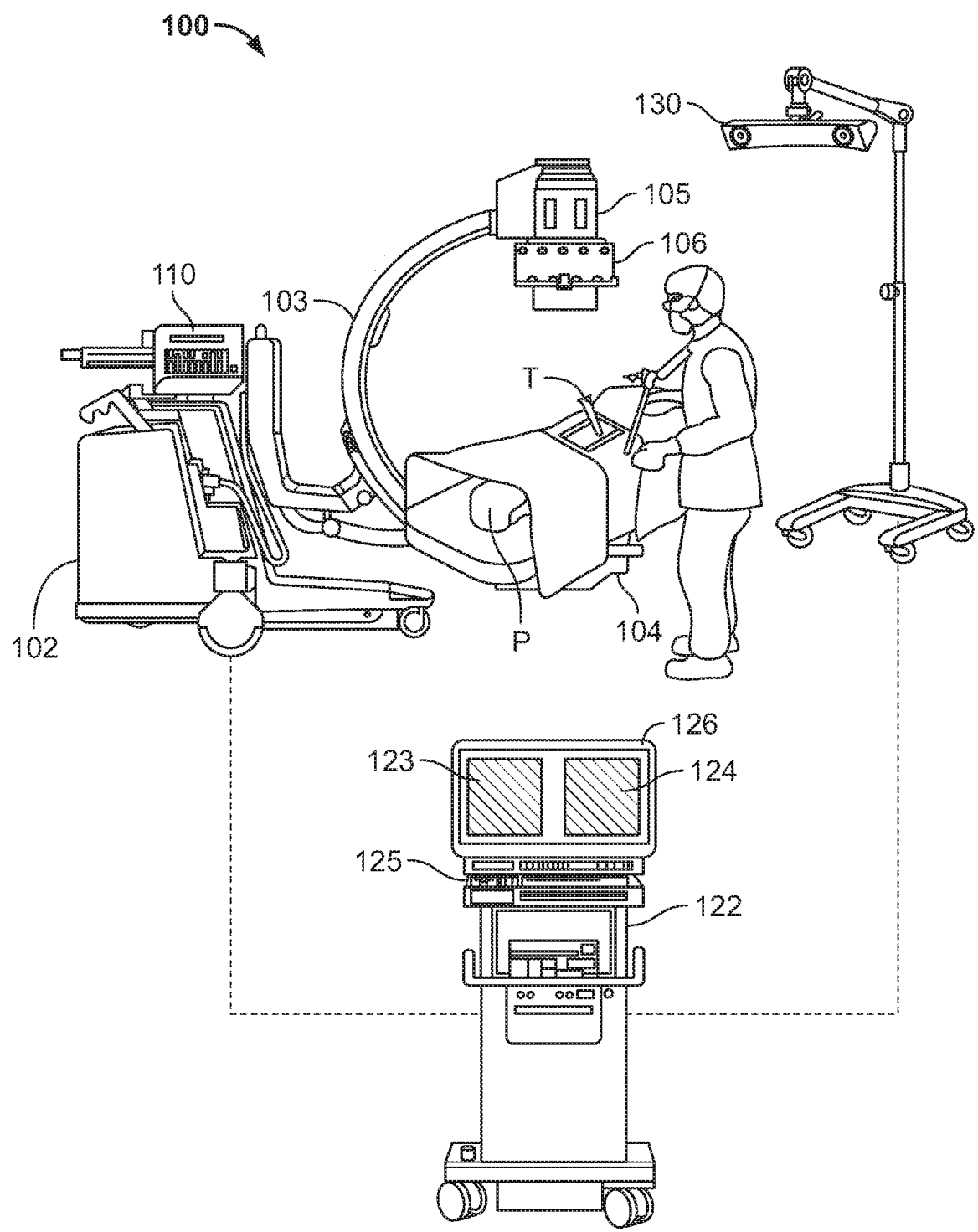
FIG. 1 illustrates an example system for performing a surgical procedure, according to an embodiment of the present disclosure.

Referring now to the figures, FIG. 1 is a diagram of an example system 100 for performing a surgical procedure. The example system 100 includes a base unit 102 supporting a C-Arm imaging device 103. The C-Arm 103 includes a radiation source 104 that is positioned beneath the patient P and that directs a radiation beam upward to the receiver 105. The receiver 105 of the C-Arm 103 transmits image data to a control unit 122. The control unit 122 may communicate with a tracking device 130 to obtain position and orientation information of various instruments (e.g., instrument T) used during the surgical procedure.

The base unit 102 includes a control panel 110 through which a user can control the location of the C-Arm 103, as well as the radiation exposure. The control panel 110 thus permits the radiology technician to acquire images of the surgical site at a surgeon's direction, control the radiation dose, and initiate a radiation pulse image.

The C-Arm 103 may be rotated about an axis parallel to the patient P for different viewing angles of the surgical site. In some instances, implants or instrument T may be situated at the surgical site, necessitating a change in viewing angle for an unobstructed view of the site. Thus, the position of the receiver relative to the patient P, and more particularly relative to the surgical site of interest, may change during a procedure as needed by the surgeon or radiologist. Consequently, the receiver 105 may include a tracking target 106 mounted thereto that allows tracking of the position of the C-Arm 103 using the tracking device 130. By way of example only, the tracking target 106 may include a plurality of infrared (IR) reflectors or emitters spaced around the target, while the tracking device 130 is configured to triangulate the position of the receiver 105 from the IR signals reflected or emitted by the tracking target 106.

The control unit 122 can include a digital memory associated therewith and a processor for executing digital and software instructions. The control unit 122 may also incorporate a frame grabber that uses frame grabber technology to create a digital image for projection as displays 123 and 124 on a display device 126. The displays 123 and 124 are positioned for interactive viewing by the surgeon during the procedure. The two displays 123 and 124 may be used to show images from two views, such as lateral and A/P, or may show a baseline scan and a current scan of the surgical site, or a current scan and a "merged" scan based on a prior baseline scan and a low radiation current scan. An input device 125, such as a keyboard or a touch screen, can allow the surgeon to select and manipulate the on-screen images. It is understood that the input device may incorporate an array of keys or touch screen icons corresponding to the various tasks and features implemented by the control unit 122. The control unit 122 includes a processor that converts the image data obtained from the receiver 105 into a digital format. In one example, the control unit 122 is configured to receive X-ray data, computed tomography imaging data, magnetic resonance imaging data, or biplanar X-ray data from a subject. In some cases, the C-Arm 103 may be operating in the cinematic exposure mode and generating many images each second. In these cases, multiple images can be averaged together over a short time period into a single image to reduce motion artifacts and noise.

In one example, the control unit 122 is configured to determine digitized positions of one or more vertebral bodies of a subject. The vertebral bodies may be, for example, cervical, thoracic, lumbar, sacrum, or coccyx. In one example, the control unit 122 includes software configured to receive, collect, and/or determine one or more digitized positions that correspond to any number of locations, respectively, to one or more vertebral bodies. In another example, the control unit 122 may collect the digitized positions from any data source of the subject that depicts the vertebral bodies in sufficient detail, including but not limited to, an X-ray image, a computed tomography image, a magnetic resonance imaging image, or biplanar X-ray image of the subject. In one example, the control unit 122 may contain image recognition software whereby the control unit 122 digitizes data provided, such as an X-ray image, a computed tomography image, a magnetic resonance imaging image, or biplanar X-ray image of the subject, and the control unit 122 may select digitized positions based on output from the image recognition software. The image recognition software, by way of example, may process the image and identify and transmit the positions, such as the corners of the one or more vertebral bodies. In some embodiments, this processing and identification is automatic, while in other embodiments, a user manually selects or verifies the positions from data provided to the control unit 122 such that the control unit 122 receives the digitized positions from the user. In yet another embodiment, the digitized positions are received digitally from a digital imaging component, such as a digital radiography system.

The tracking device 130 may include sensors for determining location data associated with a variety of elements (e.g., an infrared reflector or emitter) used in a surgical procedure. In one example, the sensors may be a charge-coupled device (CCD) image sensor. In another example, the sensors may be a complementary metal-oxide-semiconductor (CMOS) image sensor. It is also envisioned that a different number of other image sensors may be used to achieve the functionality described.

While the control unit 122 is shown in FIG. 1 in the context of a surgical system within an operating room or surgical theatre, it is contemplated that the control unit 122 may be utilized for surgical planning with an input device 125 and display device 126 without the remaining components of the system shown in FIG. 1.

Figure 2:
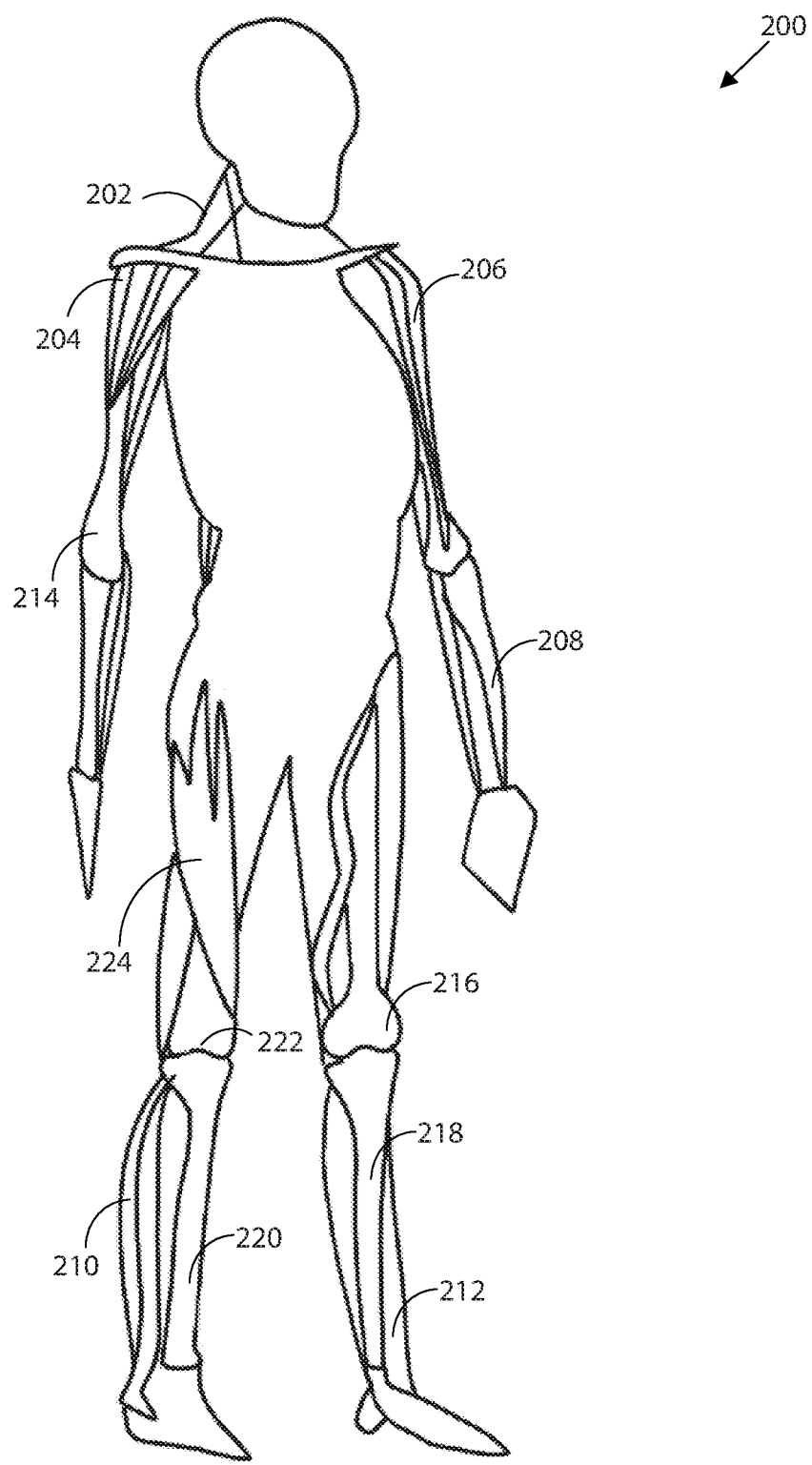
FIG. 2 illustrates an example diagram of a biomechanical model, according to an embodiment of the present disclosure.

FIG. 2 is an example diagram of a full body generic biomechanical model 200. The biomechanical model 200 includes muscles 202, 204, 206, 208, 210, 212, and 224 connected to one or more rigid body segments 214, 216, 218, 220, and 222. As shown, the biomechanical model 200 is in a standing posture. In another example, the biomechanical model 200 is in a different predetermined posture such as a sitting posture. It is envisioned that the predetermined posture can include other postures that are not described herein.

In one example, the biomechanical model 200 is a musculoskeletal model of a human subject. In one example, the musculoskeletal model includes several elements such as bones (e.g., rigid bodies), joints (e.g., mobilizers, constraints and forces), contact elements (e.g., rigid constraints and compliant forces), and ligaments and muscle actuators (e.g., forces). In one example, the elements of the musculoskeletal model are based on user-defined functions. For example, a user-defined function may be associated with a constraint such as a maximum angle between two vertebral bodies. In one example, the muscles spanning from joints are connected to bones via tendons and ligaments. By way of example, the muscles are able to generate forces and movement. In another example, the musculoskeletal model includes one or more spino-pelvic parameters, ligament parameters, muscle parameters, and joint kinematics.

According to one embodiment, the biomechanical model 200 is customized to represent patient-specific parameters. The patient-specific parameters, including, for example, body weight and height, muscle strength, and spino-pelvic parameters such as the pelvic incidence angle, sacral slope angle, and pelvic tilt are used to determine the sagittal curvature of the spine of the patient. In another example, the spino-pelvic parameters may include lumbar lordosis, thoracic kyphosis, and sagittal translation of the C7 plumbline. In another example, the spino-pelvic parameters may include relative positions and angles of vertebral bodies. In one example, the ligament parameters may include approximated slack length, and coefficients of force-length relationship.

In one example, the joint kinematics includes the relative motion between two consecutive segments of the musculoskeletal model. In one example, the analysis of two consecutive segments (e.g., rigid bodes) requires knowledge of scalar quantities to define the relative motion of the links involved. For example, the scalar quantities may be described in terms of three rotations and three translations with respect to the human anatomy. In one example, in order to analyze a joint range of motion, the joint kinematics may consider a characterization of a range of motion in one or more planes such as a sagittal plane (i.e., longitudinal plane), transverse plane (i.e., axial plane or horizontal plane), and frontal plane (i.e., coronal plane).

Figure 3:
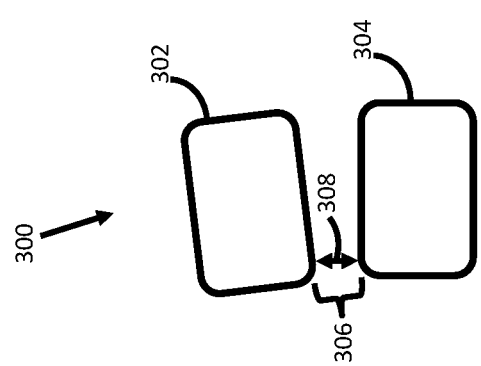
FIG. 3 illustrates an example diagram of two vertebral bodies, according to an embodiment of the present disclosure.

FIG. 3 illustrates an example diagram 300 of a patient-specific biomechanical model of two vertebral bodies 302, 304 generated from applying patient specific parameters to the generic biomechanical model 200 of FIG. 2. As shown, the two vertebral bodies 302, 304 are at given angle 306 relative to each other and given distance 308 from each other.

According to an exemplary embodiment, a radiograph of the patient is taken pre-operatively. The radiograph may be captured while the patient is in a standing posture. Alternatively, the radiograph may be captured while the patient is in a posture other than standing, such as in the prone or supine position. During surgical planning, the radiograph is transmitted to the control unit, and the control unit is configured to align one or more vertebral bodies represented in the biomechanical model 200 to one or more vertebral bodies of the preoperative radiograph of the patient, creating a patient-specific biomechanical model 200. In one example, alignment of the one or more vertebral bodies may include modifying the biomechanical model 200 to represent subject-specific spino-pelvic sagittal alignment, morphometry of vertebral bodies, body weight and height, and muscle strength (e.g., maximum allowed active force). Based on preoperative radiographs and inputs of the additional patient-specific parameters, the individual vertebrae represented in the patient-specific model 200 may be morphed to reflect the spine curvature in the sagittal plane, for example, as shown in FIG. 4.

According to another example, the radiographs of the patient may be taken intraoperatively using a system like the one shown in FIG. 1. According to this exemplary embodiment, the control unit 122 is in communication with an imaging system such as a C-Arm, and receives the radiograph of the subject acquired by the imaging system immediately prior to or during surgery. Intraoperative imaging may be used to create a patient-specific biomechanical model 200 or to update an existing patient-specific biomechanical model 200 that was created pre-operatively.

Figure 4:
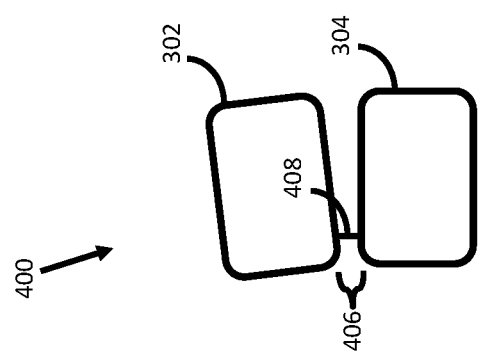
FIG. 4 illustrates another example diagram of two vertebral bodies, according to an embodiment of the present disclosure.

FIG. 4 illustrates an example diagram 400 of the two vertebral bodies 302, 304 represented by the patient-specific biomechanical model 200, which is generated from the generic biomechanical model 200 of FIG. 3 morphed according to the corresponding vertebral bodies of a preoperative radiograph of the patient. As shown in FIG. 4, the given angle 406 between the two vertebral bodies 302, 304 of the actual patient is less than the given angle 306 between the two vertebral bodies 302, 304 of the generic biomechanical model 200 shown in FIG. 3. In addition, the given distance 408 between the two vertebral bodies 302, 304 of the actual patient in FIG. 4 is less than the given height 308 between the two vertebral bodies 302, 304 of the generic biomechanical model 200 in FIG. 3. In one example, the disparity in height or disparity in angle between vertebral bodies of an actual patient versus that of a more typical spine represented by the generic biomechanical model 200 may be as a result of a pathology, such as spondylosis.

Figure 5:
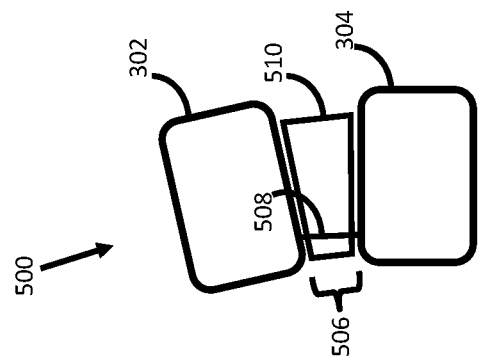
FIG. 5 illustrates an example diagram of two vertebral bodies and an implant, according to an embodiment of the present disclosure.

In one example, a control unit 122 may be configured to predict or determine how a simulated surgical correction will affect the posture of the patient post-operatively. FIG. 5 illustrates an example diagram 500 of the patient-specific biomechanical model 200 showing two vertebral bodies 302, 304 with an implant 510 positioned between the two vertebral bodies 302, 304. As shown in FIG. 5, upon insertion of the implant 510, the given angle 506 between the vertebral bodies 302, 304 is greater than the given angle 406 between the vertebral bodes 302, 304 prior to insertion of the implant 510 (FIG. 4). In addition, the given distance 508 between the two vertebral bodies 302, 304 is greater than the given distance 408 between the two vertebral bodies 302, 304 prior to insertion of the implant 510. While the exemplary embodiment is illustrated using an intervertebral implant as the surgical correction, it is contemplated that other surgical corrections using other types of implants and/or modifications to (including removal of all or portions of bone) or manipulations of a patient's spine could also be simulated with the biomechanical model.

Based on the received one or more spinal correction inputs (e.g., simulating the insertion of an implant 510) to the two vertebral bodies 302, 304 as illustrated for example in FIG. 5, the control unit 122 is configured to simulate the biomechanical model 200 in a predetermined posture. In one example, rigid constraints are applied to fused or fixed segments (e.g., vertebral bodies 302, 304 with implant 510 inserted therebetween) that allow no motion in a given plane but allow full force and moment transmission.

In one example, the control unit 122 is configured to simulate the predicted global posture of the patient taking the surgical correction inputs into consideration. By way of example, the standing body posture is modeled by controlling the horizontal position of the body center of mass over ankle joints. In this example, the global rotation of the skull is restrained to model horizontal gaze. Knee flexion, pelvic tilt, lumbar and thoracic compensation angles may be varied during posture optimization. In one example, changes to lumbar and thoracic curvature are distributed between individual segments using ratios of relative segmental mobility.

Inverse dynamics refers to the estimation of unknown forces from known displacements by solving Newtonian equations of motion for a given mechanical system in an inverse fashion. In regard to musculoskeletal modeling, some of the forces of interest are the internal muscle and joint reaction forces that are responsible for supporting body posture or motion. Due to a large number of muscles, the equations of motion do not have a unique solution based on an infinite number of combinations of muscle activations can produce the simulated body kinematics. In one example, the muscle recruitment criterion is based on a sum of cubed muscle activities. The sum of cubed muscle activities may minimize the muscle effort based on the interaction of various groups of muscles within the subject.

Figure 6:
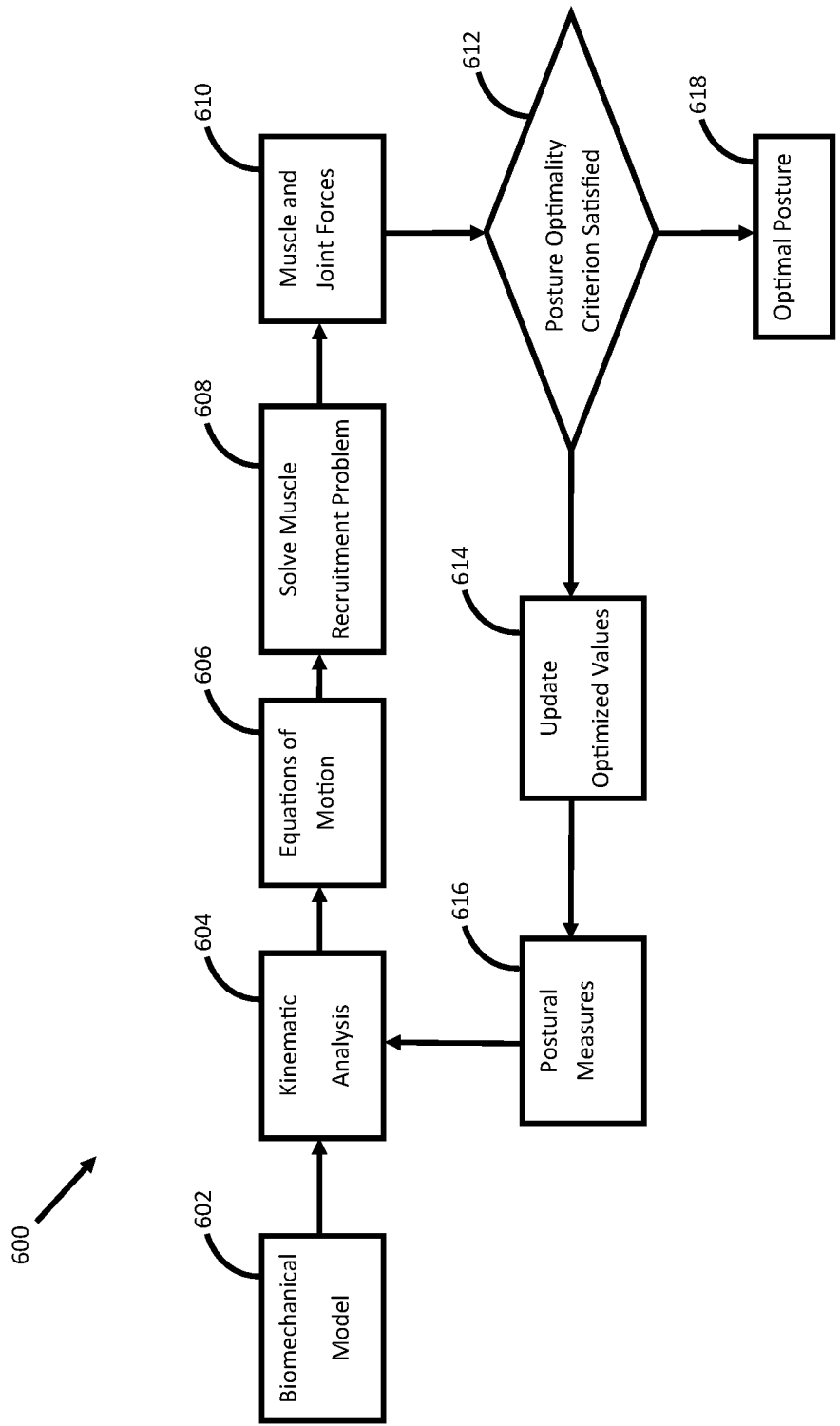
FIG. 6 illustrates an example workflow, according to an embodiment of the present disclosure.

In one example, posture prediction can be determined by using an inverse-inverse dynamics approach, as illustrated by the example workflow 600 in FIG. 6. In an inverse-inverse dynamics approach, an additional optimization loop is added to iteratively adjust kinematics (e.g., posture) based on the output of an inverse dynamics simulation. In one example, a simulation-predicted muscle effort can be used as an objective function to be minimized in an effort to find an optimal posture. By way of example, the choice of minimum muscle expenditure as a posture optimality criterion may correspond to the principle of the cone of economy (i.e., an ideal spinal alignment allows a standing posture with minimal muscular energy). In one example, during posture optimization, the angles of thoracic and lumbar compensation at unfused segments, pelvic tilt, and knew flexion are optimized simultaneously until a solution is found. In one example, the control unit 122 is configured to implement an inverse-inverse dynamics approach as depicted in the workflow 600.

Referring to FIG. 6, as shown by block 602, the control unit 122 is configured to receive a biomechanical model (e.g., biomechanical model 200) that has been customized to a patient, as described herein. In one example, a user may choose to apply one or more logic parameters such that the biomechanical model maintains a center of mass over the ankles; maintains a constant horizontal gaze; stands in a posture where postural muscle energy is minimized; has an arm position matching the patient during imaging; has no coronal plane deformity, or any combination of these logic parameters.

As shown by block 604, the control unit 122 is configured to perform a kinematic analysis. In one example, the kinematic analysis includes simulating positions, velocities and accelerations of the segments in the full body for typical activities (e.g., sitting, standing, walking, etc.) of a patient and for fundamental human body motions. In one example, the control unit is configured to simulate the surgical correction (e.g., insertion of an implant 510 between vertebral bodies 302, 304) with anatomical properties of the patient. By way of example, the anatomical properties of the patient may include size and shape of vertebral bodies, muscle attachment sites and positions of joint rotation centers.

As shown by block 606, the control unit 122 is configured to determine one or more equations of motion. In one example, the one or more equations of motion may be directed at determining one or more of a position, velocity, and acceleration of various elements of the biomechanical model 200. In another example, the one or more equations of motion may be directed at determining one or more of a force and torque acting on various elements of the biomechanical model 200.

As shown by block 608, the control unit 122 is configured to solve a muscle recruitment problem. In one example, the muscle recruitment problem may include an optimization of muscle force data or muscle activation data corresponding to one or more postures of the subject.

As shown by block 610, the control unit 122 is configured to output the muscle and joint forces as determined in the previous step of the workflow 600. As shown by block 612, the control unit 122 is configured to determine whether a posture optimality criterion has been satisfied. If the posture optimality criterion has been satisfied, then the workflow 600 ends with block 618. Otherwise, the control unit 122 proceeds to block 614 of the workflow 600. For example, the posture optimality criterion may include one or more of minimal muscle effort, minimal sagittal imbalance, and minimal loading on one or more vertebral bodies.

As shown by block 614, the control unit 122 is configured to update the optimized variables. In one example, the optimized variables may include spino-pelvic parameters, lumbar compensation, thoracic compensation, cervical compensation, pelvic tilt, hip flexion, knee flexion, ankle flexion, or position of the body center of mass.

As shown by block 616, the control unit is configured to determine one or more postural measures. For example, the postural measures may include one or more of thoracic compensation, lumbar compensation, pelvic tilt, and knee flexion.

Figure 7:
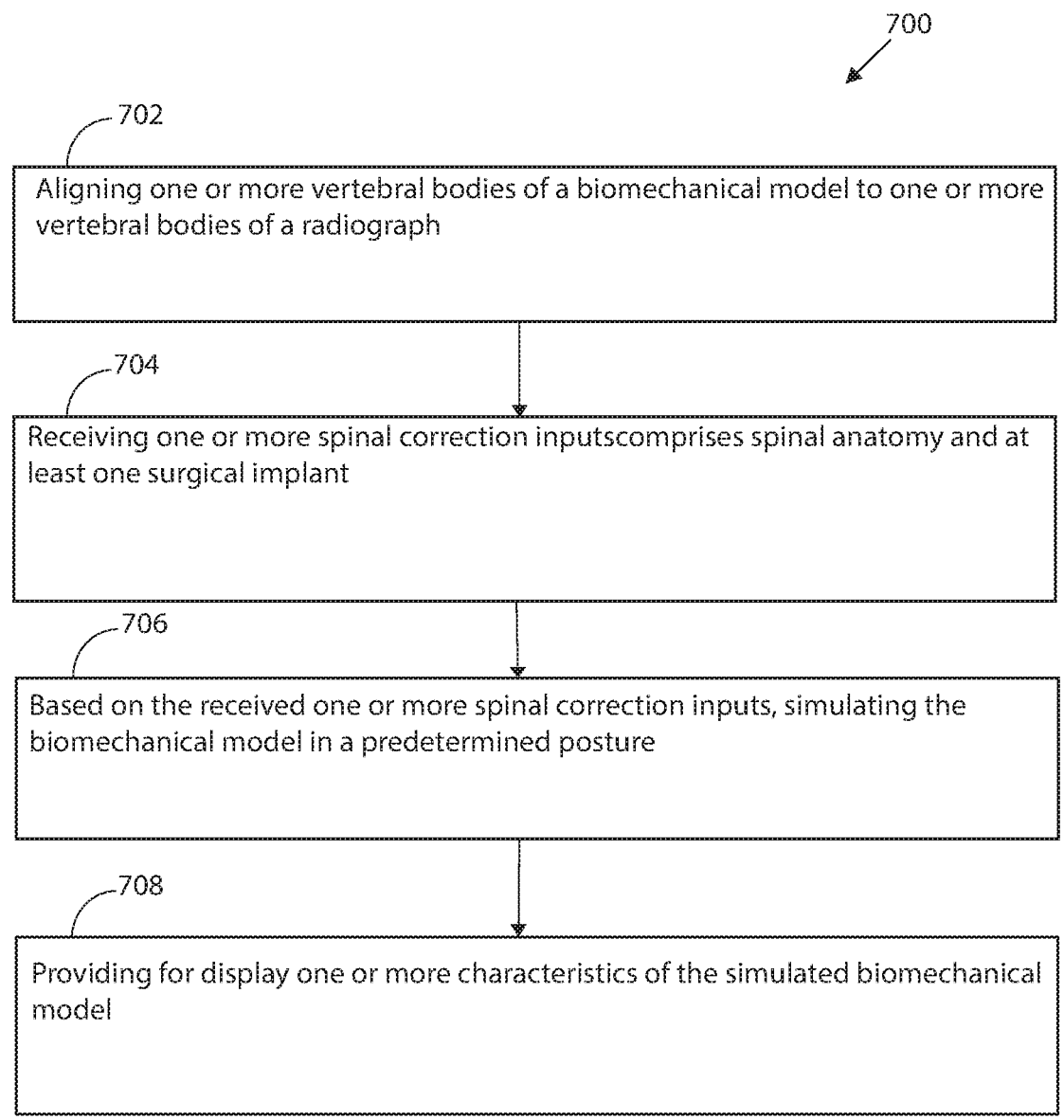
FIG. 7 illustrates an example flow diagram, according to an embodiment of the present disclosure.

FIG. 7 is a flow diagram of example method during a surgical procedure, in accordance with at least one or more embodiments described herein. Although the blocks in each figure are illustrated in a sequential order, the blocks may in some instances be performed in parallel, and/or in a different order than those described therein. Also, the various blocks may be combined into fewer blocks, divided into additional blocks, and/or removed based upon the desired implementation.

In addition, the flow diagram of FIG. 7 shows the functionality and operation of possible implementations of the present embodiment. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, each block in FIG. 7 may represent circuitry that is wired to perform the specific logical functions in the process. Illustrative methods, such as those shown in FIG. 7, may be carried out in whole in or in part by a component or components in the cloud and/or system 100 of FIG. 1. However, it should be understood that the example methods may instead be carried out by other entities or combinations of entities (i.e., by other computing devices and/or combination of computer devices), without departing from the scope of the invention. For example, functions of the methods of FIG. 7 may be fully performed by a computing device (or components of a computing device such as one or more processors), or may be distributed across multiple components of the computing device, across multiple computing devices (e.g., control unit 122 of FIG. 1), and/or across a server.

Referring to FIG. 7, an example method 700 during a surgical procedure may include one or more operations, functions, or actions as illustrated by blocks 702-708. In one embodiment, the method 700 is implemented in whole or in part by the system 100 of FIG. 1. According to another embodiment, the method 700 is implemented in whole or in part by a computing device in the operating room that may be in communication with one or more components of the system 100 of FIG. 1. According to yet another embodiment, the method 700 is implemented in whole or in part by a computing device outside of the operating room or surgical theatre, such as, for example, in a surgeon's office or any location where surgical planning takes place.

As shown by block 702, the method 700 includes aligning one or more vertebral bodies of a biomechanical model to one or more vertebral bodies of a radiograph of an actual patient. In one example, the biomechanical model comprises a musculoskeletal model of the subject. In one example, the musculoskeletal model includes one or more of spino-pelvic parameters, ligament parameters, and joint kinematics. In one example, processing of the musculoskeletal model comprises inverse-inverse dynamics modelling. In another example, the method also includes generating a sagittal curvature profile based on the one or more vertebral bodies of the radiograph. In one example, aligning the one or more vertebral bodies of the biomechanical model comprises modifying the biomechanical model to match the sagittal curvature profile. By way of example, modifying the biomechanical model may include one or more of scaling the one or more vertebral bodies, adjusting positioning of the one or more vertebral bodies, and morphing a simulated subject anatomy.

As shown by block 704, the method 700 includes receiving one or more spinal correction inputs. In one example, the one or more spinal correction inputs comprises one or more changes in intervertebral height and angle between the one or more vertebral bodies. In one example, the one or more spinal correction inputs includes simulating one or more spinal implants between one or more vertebral bodies. In another example, the one or more spinal correction inputs includes simulating the removal of one or more discs between a plurality of vertebral bodies.

As shown by block 706, the method 700 includes based on the received one or more spinal correction inputs, simulating the biomechanical model in a predetermined posture. In one example, the predetermined posture is a standing body posture. In one example, the standing body posture is determined according to a position of a center of mass within the biomechanical model. In another example, the predetermined posture is a sitting body posture.

As shown by block 708, the method 700 includes providing for display one or more characteristics of the simulated biomechanical model. In one example, the characteristics of the simulation biomechanical model may include any combination of a value of muscle activation in a patient, a value of lordosis, a value of kyphosis, and a value of Cobb angle. In another example, the one or more characteristics may include one or more values corresponding to a minimal muscle effort, minimal sagittal imbalance, and minimal loading on one or more vertebral bodies.

Figure 8:
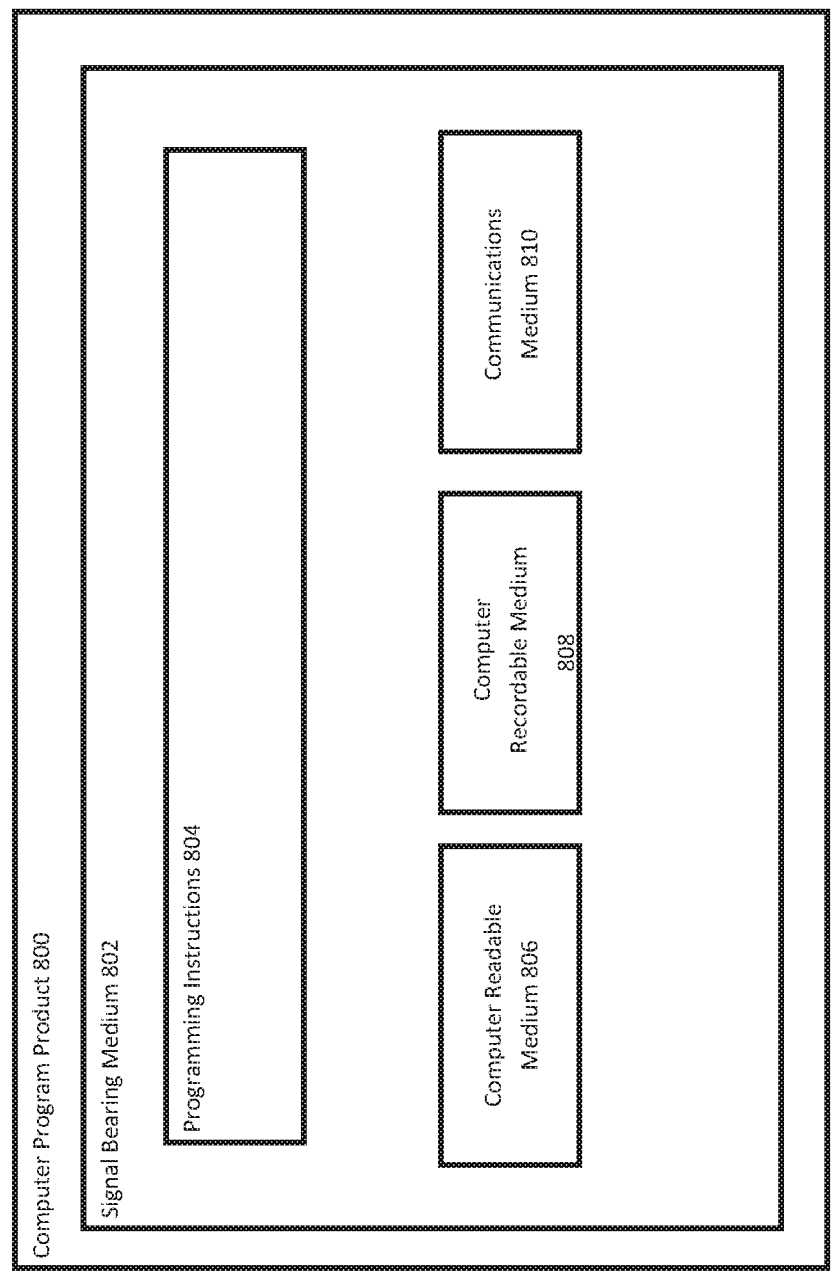
FIG. 8 illustrates an example computer readable medium, according to an embodiment of the present disclosure.

FIG. 8 depicts an example computer readable medium configured according to an example embodiment. In example embodiments, an example system may include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques may be implemented by computer program instructions encoded on a computer readable storage media in a machine-readable format, or on other media or articles of manufacture. FIG. 8 is a schematic illustrating a conceptual partial view of an example computer program product that includes a computer program for executing a computer process on a computing device, arranged according to at least some embodiments disclosed herein.

In one embodiment, an example computer program product 800 is provided using a signal bearing medium 802. The signal bearing medium 802 may include one or more programming instructions 804 that, when executed by one or more processors, may provide functionality or portions of the functionality described above with respect to FIGS. 1-7. In some examples, the signal bearing medium 802 may be a computer-readable medium 806, such as, but not limited to, a hard disk drive, a Compact Disc (CD), a Digital Video Disk (DVD), a digital tape, memory, etc. In some implementations, the signal bearing medium 702 may be a computer recordable medium 808, such as, but not limited to, memory, read/write (R/W) CDs, R/W DVDs, etc. In some implementations, the signal bearing medium 802 may be a communication medium 810 (e.g., a fiber optic cable, a waveguide, a wired communications link, etc.). Thus, for example, the signal bearing medium 802 may be conveyed by a wireless form of the communications medium 810.

The one or more programming instructions 804 may be, for example, computer executable and/or logic implemented instructions. In some examples, a computing device may be configured to provide various operations, functions, or actions in response to the programming instructions 804 conveyed to the computing device by one or more of the computer readable medium 806, the computer recordable medium 808, and/or the communications medium 810.

The computer readable medium 806 may also be distributed among multiple data storage elements, which could be remotely located from each other. The computing device that executes some or all of the stored instructions could be an external computer, or a mobile computing platform, such as a smartphone, tablet device, personal computer, wearable device, etc. Alternatively, the computing device that executes some or all of the stored instructions could be remotely located computer system, such as a server.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

What is claimed is:

1. A system for surgical planning of spinal pathology or spinal deformity correction in a subject, the system comprising:
one or more processors configured to:
align one or more vertebral bodies of a biomechanical model to one or more vertebral bodies in a radiograph of the subject, the biomechanical model being a musculoskeletal model;
process the biomechanical model, wherein processing the biomechanical model comprises inverse-inverse dynamics modelling;
receive one or more spinal correction inputs;
based on the received one or more spinal correction inputs, simulate the biomechanical model in a predetermined posture;
iteratively update the biomechanical model based on output of an inverse dynamics simulation on the model, wherein to iteratively update includes to simultaneously optimize angles of thoracic and lumbar compensation at areas not fused by the spinal correction inputs, pelvic tilt, and knee flexion until a simulation-predicted muscle effort criterion has been satisfied; and
after the muscle effort criterion has been satisfied, provide for display one or more characteristics of the simulated and updated biomechanical model.

2. The system of claim 1, wherein the one or more spinal correction inputs comprises one or more changes in intervertebral height and angle between the one or more vertebral bodies.

3. The system of claim 1, wherein the musculoskeletal model includes one or more of spino-pelvic parameters, ligament parameters, and joint kinematics.

4. The system of claim 1, wherein the one or more processors are configured to generate a sagittal curvature profile based on the one or more vertebral bodies of the radiograph.

5. The system of claim 4, wherein the alignment of the one or more vertebral bodies of the biomechanical model comprises modifying the biomechanical model to match the sagittal curvature profile.

6. The system of claim 5, wherein the modifying of the biomechanical model comprises one or more of scaling the one or more vertebral bodies, adjusting positioning of the one or more vertebral bodies, and morphing a simulated subject anatomy.

7. The system of claim 1, wherein the predetermined posture is a standing body posture.

8. The system of claim 7, wherein the standing body posture is determined according to a position of a center of mass within the biomechanical model.

9. The system of claim 1, wherein to simultaneously optimize the angles of thoracic and lumbar compensation includes to:
update the angles of thoracic and lumbar compensation until a posture optimality criterion has been satisfied.

10. The system of claim 1, wherein to simultaneously optimize the angles of thoracic and lumbar compensation includes to:
update the angles of thoracic and lumbar compensation based on an output of the inverse dynamics simulation on the model whereby a subsequent output of the inverse dynamics simulation on the model satisfies the simulation-predicted muscle effort criterion.

11. The system of claim 1, wherein to iteratively update includes to:
update one or more variables of the model, wherein the one or more variables include a variable selected from the group consisting of: a spino-pelvic parameter, a lumbar compensation variable, a thoracic compensation variable, a cervical compensation variable, a pelvic tilt variable, a hip flexion variable, a knee flexion variable, an ankle flexion variable, and a variable expressing a position of the body center of mass.

12. The system of claim 1, wherein to iteratively update includes to:
apply one or more logic parameters including any one of (i) maintaining a center of mass over the ankles, (ii) maintaining a constant horizontal gaze, (iii) standing in a posture where postural muscle energy is minimized, (iv) arm positioning matching the patient during imaging, (v) removing coronal plane deformity, or (vi) any combination of (i)-(v).

13. The system of claim 1, wherein to iteratively update includes to:
minimize a simulation-predicted muscle effort.

14. A method for surgical planning and assessment of spinal deformity correction in a subject, the method comprising:
aligning one or more vertebral bodies of a biomechanical model to one or more vertebral bodies of a radiograph, wherein the biomechanical model is a musculoskeletal model;
receiving one or more spinal correction inputs;
based on the received one or more spinal correction inputs, simulating the biomechanical model in a predetermined posture, wherein the simulating includes performing inverse-inverse dynamics modelling;
iteratively updating the biomechanical model based on output of an inverse dynamics simulation on the model, wherein to iteratively update includes to simultaneously optimize angles of thoracic and lumbar compensation at areas not fused by the spinal correction inputs, pelvic tilt, and knee flexion until a simulation-predicted muscle effort criterion has been satisfied; and
after the muscle effort criterion has been satisfied, providing for display one or more characteristics of the simulated and updated biomechanical model.

15. The method of claim 14, wherein the one or more spinal correction inputs comprises one or more changes in intervertebral height and angle between the one or more vertebral bodies.

16. The method of claim 14, wherein the musculoskeletal model includes one or more of spino-pelvic parameters, ligament parameters, and joint kinematics.

17. The method of claim 14, wherein the method further comprises:
generating a sagittal curvature profile based on the one or more vertebral bodies of the radiograph.

18. The method of claim 17, wherein aligning the one or more vertebral bodies of the biomechanical model comprises modifying the biomechanical model to match the sagittal curvature profile.

19. The method of claim 18, wherein the modifying of the biomechanical model comprises one or more of scaling the one or more vertebral bodies, adjusting positioning of the one or more vertebral bodies, and morphing a simulated subject anatomy.

20. The method of claim 14, wherein the predetermined posture is a standing body posture.

21. The method of claim 20, wherein the standing body posture is determined according to a position of a center of mass within the biomechanical model.

22. The method of claim 14, wherein to iteratively update includes to:
update one or more variables of the model, wherein the one or more variables include a variable selected from the group consisting of: a spino-pelvic parameter, a lumbar compensation variable, a thoracic compensation variable, a cervical compensation variable, a pelvic tilt variable, a hip flexion variable, a knee flexion variable, an ankle flexion variable, and a variable expressing a position of the body center of mass.

23. The method of claim 14, wherein to iteratively update includes to:
apply one or more logic parameters including any one of (i) maintaining a center of mass over the ankles, (ii) maintaining a constant horizontal gaze, (iii) standing in a posture where postural muscle energy is minimized, (iv) arm positioning matching the patient during imaging, (v) removing coronal plane deformity, or (vi) any combination of (i)-(v).

24. The method of claim 14, wherein to iteratively update includes to:
minimize a simulation-predicted muscle effort.

25. The method of claim 14, wherein to simultaneously optimize the angles of thoracic and lumbar compensation includes to:
update the angles of thoracic and lumbar compensation until a posture optimality criterion has been satisfied.

26. The method of claim 14, wherein to simultaneously optimize the angles of thoracic and lumbar compensation includes to:
update the angles of thoracic and lumbar compensation based on an output of the inverse dynamics simulation on the model whereby a subsequent output of the inverse dynamics simulation on the model satisfies the simulation-predicted muscle effort criterion.

* * * * *